US009326950B2

(12) United States Patent
Tarasova et al.

(10) Patent No.: US 9,326,950 B2
(45) Date of Patent: May 3, 2016

(54) SELF-ASSEMBLING NANOPARTICLES COMPOSED OF TRANSMEMBRANE PEPTIDES AND THEIR APPLICATION FOR SPECIFIC INTRA-TUMOR DELIVERY OF ANTI-CANCER DRUGS

(75) Inventors: Nadya I. Tarasova, Frederick, MD (US); Sergey G. Tarasov, Frederick, MD (US); Christopher J. Michejda, North Potomac, MD (US); Maria J. Michejda, legal representative, North Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 966 days.

(21) Appl. No.: 12/513,950

(22) PCT Filed: Nov. 6, 2007

(86) PCT No.: PCT/US2007/083772
§ 371 (c)(1),
(2), (4) Date: Sep. 22, 2009

(87) PCT Pub. No.: WO2008/058125
PCT Pub. Date: May 15, 2008

(65) Prior Publication Data
US 2010/0034896 A1  Feb. 11, 2010

Related U.S. Application Data

(60) Provisional application No. 60/864,665, filed on Nov. 7, 2006.

(51) Int. Cl.
*A61K 9/51* (2006.01)

(52) U.S. Cl.
CPC .................. *A61K 9/5169* (2013.01)

(58) Field of Classification Search
None
See application file for complete search history.

(56) References Cited

U.S. PATENT DOCUMENTS

| | | | |
|---|---|---|---|
| 6,187,775 | B1 | 2/2001 | Michejda et al. |
| 6,664,263 | B2 | 12/2003 | Cholody et al. |
| 7,105,488 | B1 | 9/2006 | Tarasova et al. |
| 2003/0170826 | A1* | 9/2003 | Rabinovich et al. .......... 435/69.7 |
| 2007/0009441 | A1* | 1/2007 | Erathodiyil et al. .......... 424/9.34 |
| 2010/0034896 | A1* | 2/2010 | Tarasova et al. .............. 424/499 |

FOREIGN PATENT DOCUMENTS

| | | | |
|---|---|---|---|
| WO | 99/43711 A1 | 9/1999 | |
| WO | WO 9943711 A1 * | 9/1999 | ............. A61K 38/19 |
| WO | 01/36477 A2 | 5/2001 | |
| WO | 01/93836 A2 | 12/2001 | |

OTHER PUBLICATIONS

Keyes-Baig, et al. ("Self-assembling Peptide as a Potential Carrier of Hydrophobic Compounds," Journal of the American Chemical Society, 126 (24): 7522-7532 (2004)).*
Tarasova et al., Inhibition of G-protein-coupled Receptor Function by Disruption of Transmembrane Domain Interactions. 1999, J. Biol. Chem. 274:34911-34915 (Applicant, deemed first to disclose present 24mer CXCR4 peptide SEQ ID No. 1; as also cited in Rabinovich et al. US20030170826, Table 2.).*
ChemSpider, http://www.chemspider.com/Chemical-Structure.10368587.html, 2015.*
Keyes-Baig, et al., "Self-assembling Peptide as a Potential Carrier of Hydrophobic Compounds," *Journal of the American Chemical Society*, 126 (24): 7522-7532 (2004).
Okabayashi et al., "The Self-Assembly of Oligopeptides," *Self-Assembly*: 331-338 (2003).
Dennison et al., "VSV transmembrane domain (TMD) peptide promotes PEG-mediated fusion of liposomes in a conformationally sensitive fashion," *BioChemistry*, 41, 14925-14934 (2002).
George et al., "A transmembrane domain-derived peptide inhibits D1 dopamine receptor function without affecting receptor oligomerization," *J. Biol. Chem.*, 273 (46), 30244-30248 (1998).
George et al., "Blockade of G protein-coupled receptors and the dopamine transporter by a transmembrane domain peptide: novel strategy for functional inhibition of membrane proteins in vivo," *J. Pharmacol. Exp. Ther.*, 307 (2), 481-489 (2003).
Hebert et al., "A peptide derived from a beta2-adrenergic receptor transmembrane domain inhibits both receptor dimerization and activation," *J. Biol. Chem.*, 271 (27), 16384-16392 (1996).
Kimura et al., "Molecular assembly formation in solution of spiral forming," *Kyoto Daigaku Nippon Kagaku Sen'I Kenkyusho Koenshu.*, 59, 65-70, abstract (2002).
Koga et al., "Alpha-helical nanoparticle from a poly(leucine)-poly(ethylene glycol) amphiphilic block copolymer containing cross-linking sites and its structural stabilisation," *Science and Engineering Review of Doshisha University*, 47 (3), 185-191, abstract (2006).

(Continued)

*Primary Examiner* — Maury Audet
(74) *Attorney, Agent, or Firm* — Leydig, Voit & Mayer

(57) ABSTRACT

The invention provides a method of handling a hydrophobic agent, which method comprises (a) combining in an aqueous solution (i) a hydrophobic agent and (ii) an isolated peptide that is a structural analog of a transmembrane domain of an integral membrane protein, wherein one terminus of the peptide has one or more negatively charged residues, and (b) allowing the peptide to self-assemble into nanoparticles, wherein the nanoparticles comprise the hydrophobic agent.

15 Claims, 4 Drawing Sheets

(56) References Cited

OTHER PUBLICATIONS

Kojima et al., "The preparation of self-organized nano-particles composed of peptide-based amphiphiles and the optical resolution properties," *Transactions of the Materials Research Society of Japan*, 28 (3), 585-588 (2003).

Rösler et al., "Advanced drug delivery devices via self assembly of aphiphilic block copolymers," *Advanced Drug Delivery Reviews*, 53, 95-108 (2001).

Tarasova et al., "Bisimidazoacridones: effect of molecular environment on conformation and photophysical properties," *Photochem. Photobiol.*, 70 (4), 568-578 (1999).

Tarasova et al., "Inhibition of G-protein-coupled receptor function by disruption of transmembrane domain interactions," *J. Biol. Chem.*, 274 (49), 34911-34915 (1999).

Tarasova et al., "Transmembrane inhibitors of P-glycoprotein, an ABC transporter," *J. Med. Chem.*, 48, 3768-3775 (2005).

Tourand et al., "Nanoparticles of amphiphilic block copolyaminoacid: complexation and release of insulin," *Proceedings of the International Symposium on Controlled Release of Bioactive*, 26th, 26-27 (1999).

Tu et al., "Liposomal targeting through peptide-amphiphile functionalization," *American Pharmaceutical Review*, 7 (2), 36-41 (2004).

Tarasov et al., "Structural plasticity of a transmembrane peptide allows self-assembly into biologically active nanoparticles," *Proceedings of the National Academy of Sciences USA*, 108(24): 9798-9803, (2011).

* cited by examiner

```
                        SEQUENCE LISTING

<160> NUMBER OF SEQ ID NOS: 9

<210> SEQ ID NO 1
<211> LENGTH: 24
<212> TYPE: PRT
<213> ORGANISM: Artificial
<220> FEATURE:
<223> OTHER INFORMATION: Synthetic

<400> SEQUENCE: 1

Leu Leu Phe Val Ile Thr Leu Pro Phe Trp Ala Val Asp Ala Val Ala
1               5                   10                  15

Asn Trp Tyr Phe Gly Asn Asp Asp
            20

<210> SEQ ID NO 2
<211> LENGTH: 25
<212> TYPE: PRT
<213> ORGANISM: Artificial
<220> FEATURE:
<223> OTHER INFORMATION: Synthetic

<400> SEQUENCE: 2

Asp Asp Thr Arg Tyr Ala Tyr Tyr Tyr Ser Gly Ile Gly Ala Gly Val
1               5                   10                  15

Leu Val Ala Ala Tyr Ile Gln Val Ser
            20                  25

<210> SEQ ID NO 3
<211> LENGTH: 25
<212> TYPE: PRT
<213> ORGANISM: Artificial
<220> FEATURE:
<223> OTHER INFORMATION: Synthetic

<400> SEQUENCE: 3

Leu Ile Tyr Ala Ser Tyr Ala Leu Ala Phe Trp Tyr Gly Thr Thr Leu
1               5                   10                  15

Val Leu Ser Gly Glu Gly Ser Asp Asp
            20                  25

<210> SEQ ID NO 4
<211> LENGTH: 23
<212> TYPE: PRT
<213> ORGANISM: Artificial
<220> FEATURE:
<223> OTHER INFORMATION: Synthetic

<400> SEQUENCE: 4

Asp Ser Phe Glu Asp Val Leu Leu Val Phe Ser Ala Val Val Phe Gly
1               5                   10                  15

Ala Met Ala Val Gly Gln Val
            20

<210> SEQ ID NO 5
<211> LENGTH: 23
<212> TYPE: PRT
<213> ORGANISM: Artificial
```

```
<220> FEATURE:
<223> OTHER INFORMATION: Synthetic

<400> SEQUENCE: 5

Ile Phe Gly Ile Thr Phe Ser Phe Thr Gln Ala Met Met Tyr Phe Ser
1               5                   10                  15

Tyr Ala Gly Cys Phe Asp Asp
            20

<210> SEQ ID NO 6
<211> LENGTH: 24
<212> TYPE: PRT
<213> ORGANISM: Artificial
<220> FEATURE:
<223> OTHER INFORMATION: Synthetic

<400> SEQUENCE: 6

Leu Leu Phe Val Ile Thr Leu Pro Phe Trp Ala Val Asp Ala Val Ala
1               5                   10                  15

Asn Trp Tyr Phe Gly Asn Lys Lys
            20

<210> SEQ ID NO 7
<211> LENGTH: 22
<212> TYPE: PRT
<213> ORGANISM: Artificial
<220> FEATURE:
<223> OTHER INFORMATION: Synthetic

<400> SEQUENCE: 7

Phe Val Ile Thr Leu Pro Phe Trp Ala Val Asp Ala Val Ala Asn Trp
1               5                   10                  15

Tyr Phe Gly Asn Asp Asp
            20

<210> SEQ ID NO 8
<211> LENGTH: 19
<212> TYPE: PRT
<213> ORGANISM: Artificial
<220> FEATURE:
<223> OTHER INFORMATION: Synthetic

<400> SEQUENCE: 8

Thr Leu Pro Phe Trp Ala Val Asp Ala Val Ala Asn Trp Tyr Phe Gly
1               5                   10                  15

Asn Asp Asp

<210> SEQ ID NO 9
<211> LENGTH: 11
<212> TYPE: PRT
<213> ORGANISM: Artificial
<220> FEATURE:
<223> OTHER INFORMATION: Synthetic

<400> SEQUENCE: 9

Ala Val Ala Asn Trp Tyr Phe Gly Asn Asp Asp
1               5                   10
```

SELF-ASSEMBLING NANOPARTICLES COMPOSED OF TRANSMEMBRANE PEPTIDES AND THEIR APPLICATION FOR SPECIFIC INTRA-TUMOR DELIVERY OF ANTI-CANCER DRUGS

CROSS-REFERENCE TO RELATED APPLICATIONS

This patent application is a U.S. National Phase of International Patent Application No. PCT/US2007/083772, filed Nov. 6, 2007, which claims the benefit of U.S. Provisional Patent Application No. 60/864,665, filed Nov. 7, 2006, which is incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,998 Byte ASCII (Text) file named "704615_ST25.txt," created on May 4, 2009.

BACKGROUND OF THE INVENTION

Liposomes have been evaluated both clinically and experimentally as a delivery system for administering hydrophobic agents and for mitigating the toxic effects associated with administration of anti-cancer drugs such as doxorubicin, vincristine, amphotericin, and retinoids. The potential advantages of liposome delivery include increased activity due to specific targeting, sequestration of the drug at the target site, protection of the drug from rapid metabolism, amplified therapeutic effect due to packaging of numerous drug molecules in each liposome, and decreased toxicity due to altered pharmacokinetics.

Liposomal preparations of anti-cancer agents have been shown to possess reduced toxicity and enhanced efficacy compared to "naked" drugs. Several liposomal forms of anti-tumor agents have been approved by the FDA for anti-cancer therapy. However, wider use of liposomes is hampered by difficulties in industrializing the manufacture of liposomes, along with liposomes' lack of stability and reproducibility.

An alternative delivery system that exhibits the advantageous properties of liposomes, as well as superior stability, uniformity, ease of use, and reproducibility of preparation, and that offers smaller size particles than liposomes is needed for administration of hydrophobic agents, such as anti-cancer agents. The invention provides such a delivery system and a method of using the system (e.g., for delivery of hydrophobic agents, such as anti-cancer agents, to a subject). These and other objects and advantages of the invention, as well as additional inventive features, will be apparent from the description of the invention provided herein.

BRIEF SUMMARY OF THE INVENTION

The invention provides a method of handling a hydrophobic agent, which method comprises (a) combining in an aqueous solution (i) a hydrophobic agent and (ii) an isolated peptide that is a structural analog of a transmembrane domain of an integral membrane protein, wherein one terminus of the peptide has one or more negatively charged residues, and (b) allowing the peptide to self-assemble into nanoparticles, wherein the nanoparticles comprise the hydrophobic agent.

BRIEF DESCRIPTION OF THE SEVERAL VIEWS OF THE DRAWING(S)

Figure 3:
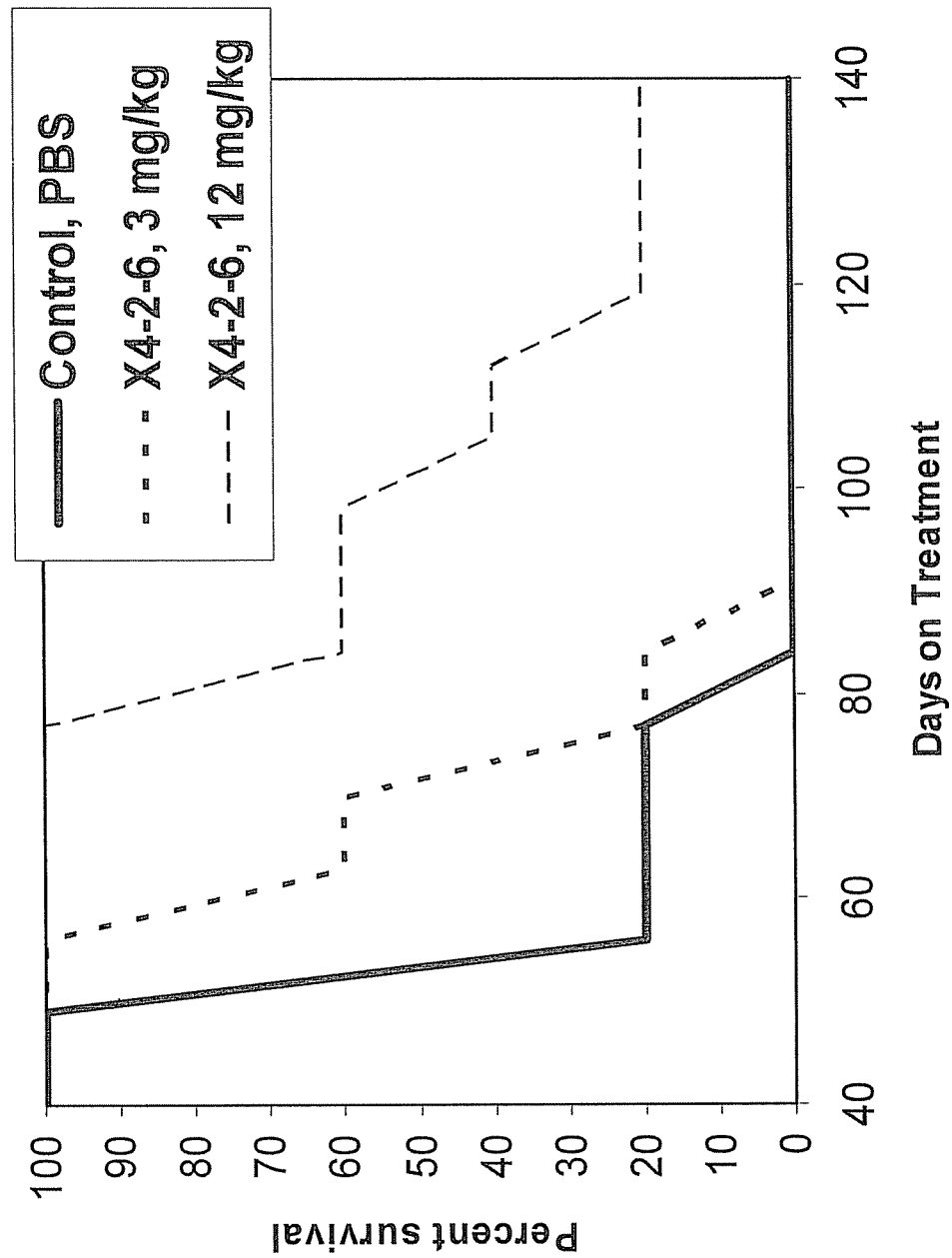

FIG. 3 is a graph of percent survival (%) versus days on treatment for three groups of nude mice intravenously injected with one million MDA-MB-231 breast cancer cells. On the day following the intravenous injection with the breast cancer cells and continuing twice weekly, the mice were intraperitoneally injected with (1) PBS only (Control); (2) 3 mg/kg of nanoparticles of SEQ ID NO: 1-PEG27 dissolved in PBS (X4-4-6, 3 mg/kg); or (3) 12 mg/kg of nanoparticles of SEQ ID NO: 1-PEG27 dissolved in PBS (X4-4-6, 12 mg/kg).

Figure 4:
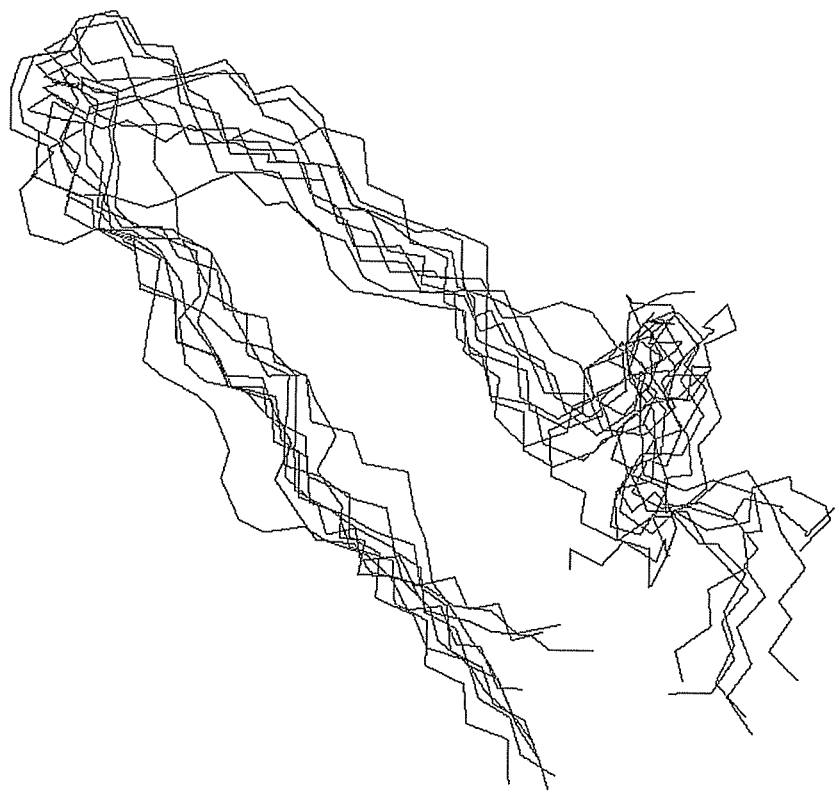

FIG. 4 is a representation of the structure of a CXCR4 peptide inside nanoparticles (SEQ ID NO: 1-PEG27) as determined by high resolution NMR.

DETAILED DESCRIPTION OF THE INVENTION

The invention is directed to the use of self-assembling nanoparticles composed of transmembrane (TM) domains of integral membrane proteins for the delivery of hydrophobic agents, such as anti-cancer agents. The TM domains of integral membrane proteins were previously considered to be highly hydrophobic peptides (see, e.g., International Patent Application Publications WO 99/43711 and WO 01/36477 and U.S. Pat. No. 7,105,488). However, it was surprisingly discovered that, when placed in aqueous solution, peptides corresponding to the TM domains of integral membrane proteins self-assemble into stable nanoparticles (micelles).

The nanoparticles are formed by allowing an isolated peptide that is a structural analog of a TM domain of an integral membrane protein to self-assemble into nanoparticles. A "structural analog of TM domain" (herein referred to as a "TM peptide") refers to a peptide that is identical or substantially identical to a portion of a TM domain of an integral membrane protein. The TM peptide preferably comprises at least about 10 amino acids (e.g., about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, or ranges thereof) that are identical or substantially identical to an amino acid sequence of a TM domain of an integral membrane protein. A TM peptide that is "substantially identical" includes one or more (e.g., 2, 3, 4, 5, 6, 7, 8, 9, 10, 11, 12, 13, 14, 15, or ranges thereof) conservative amino acid substitutions of a portion of the TM domain of an integral membrane protein.

The TM peptide desirably has one terminus that has one or more negatively charged residues (e.g., 1, 2, 3, 4, 5, 6, 7, 8, 9, 10, or more, and ranges thereof). When the terminus contains more than one negatively charged residues, preferably the negatively charged residues are consecutive. The negative charges can be provided by any suitable manner, such as by the presence of aspartate or glutamate residues at one terminus of the peptide (e.g., by addition of the residues). Substitution of the negative charges with positive charges results in the formation of much larger particles with highly variable diameters. Thus, while not wishing to be bound by any particular theory, it is believed that the presence of the negatively charged residues (e.g., two aspartate residues) allows the nanoparticles to be uniform in shape and size. Preferably, the negative charges are present at the C-terminus of the peptide.

While not wishing to be bound by any particular theory, it is believed that the TM peptide self-assembles by forming a β-loop structure in aqueous solutions. The loops associate by a mechanism that is similar to that of amyloid peptide in amyloid fibrils. Negative charges and a short C-terminal α-helix force the curvature and define the round shape of TM peptide nanostructure. A representation of the structure of a CXCR4 peptide in nanoparticles by high resolution NMR is set forth in FIG. 4.

Preferably, the TM peptide is combined with a hydrophobic agent, such as an anti-cancer agent, which agent is then encompassed within the hydrophobic center of the nanoparticles. The entrapment of the hydrophobic agents in the nanoparticles allows for the administration of the hydrophobic agents (e.g., anti-cancer agents), which are usually insoluble under physiological conditions, to subjects, wherein the agents concentrate in tumors due to enhanced permeability and retention effects.

Accordingly, the invention is directed to a method of handling a hydrophobic agent, which method comprises (a) combining in an aqueous solution (i) a hydrophobic agent and (ii) an isolated peptide that is a structural analog of a transmembrane domain of an integral membrane protein, wherein one terminus of the peptide has one or more negatively charged residues, and (b) allowing the peptide to self-assemble into nanoparticles, wherein the nanoparticles comprise the hydrophobic agent.

The TM peptide also can comprise a hydrophilic oligomer, such as polyethylene glycol (PEG), undecaethylene glycol, polystyrene, polyamino acids (e.g., polyglycine), and combinations thereof. Preferably, the hydrophilic resin is added to the same termini that contains the negative charge. While not wishing to be bound by any particular theory, it is believed that the addition of the hydrophilic oligomer to the TM peptide prevents aggregation and promotes formation of particles of uniform shape and a size that is ideally suited for, for example, tumor penetration.

The hydrophilic oligomer added to the TM peptide can be any suitable length. When the hydrophilic oligomer added is PEG, PEG5 or greater (e.g., PEG10, PEG11, PEG12, PEG15, PEG20, PEG25, PEG27, PEG30, PEG35, PEG38, PEG39, PEG40, PEG45, and ranges thereof) preferably is used. Ideally, PEG is composed of about 12 to about 27 monomeric units. When the hydrophilic oligomer added is polyglycine, 3 or greater (e.g., 4, 5, 6, 7, 8, 9, 10, 15, 20, 25, 30, 35, or ranges thereof) polyglycines preferably are used. Ideally, polyglycine of about 10 to about 20 residues is used. Notably, polyglycine tails are more effective at reducing aggregation as compared to PEG tails of comparable length.

The nanoparticles can have any suitable diameter. Preferably, the nanoparticles have a diameter of about 3 nm to about 50 nm (e.g., about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, and ranges thereof). More preferably, the nanoparticles have a diameter of about 8 nm to about 20 nm.

The TM peptide that forms the nanoparticles can be any suitable length. Preferably, the TM peptide comprises about 10 to about 50 amino acids (e.g., about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45 amino acids, or ranges thereof) in length. In more preferred embodiments, the TM peptide is about 10 to about 30 (e.g., about 15 to about 30) amino acids in length. In even more preferred embodiments, the TM peptide is about 20 to about 25 amino acids in length, and in the most preferred embodiments, the TM poly peptide is about 22 to about 25 amino acids in length. As shown in Example 3, aggregation of the nanoparticles decreases with decreased length of the TM peptide.

The TM peptide can be a portion of any suitable integral membrane protein. Examples of suitable integral membrane proteins include G protein-coupled receptor (GPCR) family members, such as CXCR4, CCR5, CCKAR, dopamine transporter (DAT), D1 dopamine receptor (D1DR), D2 dopamine receptor, $\alpha_1$-adrenergic receptor, $\beta_1$-adrenergic receptor, $\beta_2$-adrenergic receptor, and V2 vasopressin receptor (see, e.g., Herbert et al., *J. Biol. Chem.*, 271: 16384-16392 (1996); George et al., *J. Biol. Chem.*, 273:30244-30248 (1998); Tarasova et al., *J. Biol. Chem.*, 274(49): 34911-34915 (1999); and George et al., *J. Pharmacol. Exp. Ther.*, 307: 481-489 (2003); U.S. Pat. No. 7,105,488; and International Patent Application Publication WO 99/43711), and ABC transporter proteins, such as P-glycoprotein (P-gp or MDR1), MRP1, MRP2, and BCRP/ABCG2 (see, e.g., Tarasova et al., *J. Med. Chem.*, 48: 3768-3775 (2005); International Patent Application Publication WO 01/36477).

Nanoparticles constructed from the TM domains of certain receptors and transporters have their own biological activity, such as the ability to inhibit metastasis and/or angiogenesis (e.g., CXCR4 TM domains) or the ability to inhibit drug resistance of cancer cells (P-gp and ABCG2 TM domains). As such, the nanoparticles of the invention can be administered alone or with a hydrophobic agent entrapped within the hydrophobic center of the nanoparticles. When the nanoparticles are administered with a hydrophobic agent (e.g., an anti-cancer agent), the combination of the two biologically active agents (the nanoparticles themselves and the entrapped hydrophobic agent) offers the advantage of dual activity. In other words, unlike liposomes, which offer only a delivery device, the nanoparticles of the invention have their own activity, such as reducing the drug resistance of cancer cells, inhibiting the movement of cancer cells, and inhibiting the growth of blood vessels in a tumor's environment.

Suitable TM peptides include those described in International Patent Application Publications WO 99/43711 and WO 01/36477 and U.S. Pat. No. 7,105,488, as well as Leu-Leu-Phe-Val-Ile-Thr-Leu-Pro-Phe-Trp-Ala-Val-Asp-Ala-Val-Ala-Asn-Trp-Tyr-Phe-Gly-Asn-Asp-Asp (SEQ ID NO: 1; CXCR4-8), Asp-Asp-Thr-Arg-Tyr-Ala-Tyr-Tyr-Tyr-Ser-Gly-Ile-Gly-Ala-Gly-Val-Leu-Val-Ala-Ala-Tyr-Ile-Gln-Val-Ser (SEQ ID NO: 2; MDR1-2), Leu-Ile-Tyr-Ala-Ser-Tyr-Ala-Leu-Ala-Phe-Trp-Tyr-Gly-Thr-Thr-Leu-Val-Leu-Ser-Gly-Glu-Gly-Ser-Asp-Asp (SEQ ID NO: 3; MDR1-5), Asp-Ser-Phe-Glu-Asp-Val-Leu-Leu-Val-Phe-Ser-Ala-Val-Val-Phe-Gly-Ala-Met-Ala-Val-Gly-Gln-Val (SEQ ID NO: 4; MDR1-12), and Ile-Phe-Gly-Ile-Thr-Phe-Ser-Phe-Thr-Gln-Ala-Met-Met-Tyr-Phe-Ser-Tyr-Ala-Gly-Cys-Phe-Asp-Asp (SEQ ID NO: 5; MDR1-11).

Any suitable hydrophobic agents can be used with the nanoparticles. Suitable hydrophobic agents include those that can be used pharmaceutically, agriculturally, or industrially. These include biologically active or otherwise useful molecules, pharmaceuticals, imaging agents, and manufacturing reagents, as well as precursors and prodrugs of such substances. Preferred hydrophobic agents are those with biological activity or other utility in humans and other living organisms, such as humans. These include agents that are therapeutics in medicine. Examples of such agents include analgesic and anti-inflammatory agents, anesthetics, anti-adrenergic and antarrhythmics, antibiotics, anticholinergic and cholinomimetic agents, anticonvulsant agents, antidepressants, anti-epileptics, antifungal and antiviral agents, antihypertensive agents, antimuscarinic and muscarinic agents, antineoplastic agents (i.e., anti-cancer agents), antipsychotic agents, anxiolytics, hormones, hypnotics and sedatives, immunosuppressive and immunoactive agents, neuroleptic agents, neuron blocking agents, and nutrients, as well as combinations thereof.

Preferably, the hydrophobic agent for use in the inventive methods is an anti-cancer agent. Suitable anti-cancer agents include taxanes (e.g, paclitaxel and docetaxel), doxorubicin, vincristine, amphotericin, cisplatin, carboplatin, retinoids, imidazoacridones, bisimidazoacridones, camptothecin, topotecan, geldanamycin, etoposide, azonifide, and combinations thereof.

The nanoparticles can comprise targeting agents (e.g., ligands or cell receptors) to direct the nanoparticles to particular locations. For example, ligands that bind cell surface receptors overexpressed in tumor cells can be added to the nanoparticles in order to target specific tumor cells. Suitable ligands include, for example, antibodies and polypeptides that bind to the epidermal growth factor receptor (EGFR), somatostatin receptor (SSTR), insulin-like growth factor receptor, folic acid-receptor, HER2 receptor, interleukin-13 receptor, gastrin-releasing peptide receptor, CD30, vasoactive intestinal peptide receptor, gastrin receptor, prostate-specific antigen, and estrogen receptor.

The method of the invention also can comprise administering the nanoparticles comprising the hydrophobic agent (e.g., an anti-cancer agent) to a subject. Suitable subjects include mammals, such as mice, rats, rabbits, ferrets, guinea pigs, hamsters, cats, dogs, pigs, goats, cows, horses, primates, and humans.

The nanoparticles can be administered alone or in a composition. When the nanoparticles are administered in a composition, the composition preferably is a pharmaceutical (e.g., physiologically acceptable) composition. The composition comprises a carrier (e.g., a pharmaceutically or physiologically acceptable carrier) and the nanoparticles. Any suitable carrier (e.g., water, saline, and PBS) can be used within the context of the invention, and such carriers are well known in the art. The choice of carrier will be determined, in part, by the particular site to which the composition is to be administered and the particular method used to administer the composition. Suitable carriers, as well as other components suitable for use in the composition of the invention, are known in the art (e.g., *Remington's Pharmaceutical Sciences*, 17th ed., (Mack Publishing Company, Philadelphia, Pa.: 1985)). Additionally, the composition can comprise additional active agents, such as anti-cancer agents.

The nanoparticles and composition thereof can be administered to a subject to treat or prevent particular disorders and diseases. For example, when the hydrophobic agent is an anti-cancer drug, the invention encompasses the chemotherapeutic treatment of cancer, such as by methods of inhibiting tumor growth (e.g., inhibiting the proliferation, invasiveness, or metastasis of tumor cells, slowing the growth of tumors, completely halting the growth of tumors, and reducing the size of tumors) and methods of promoting the sensitivity of cancer (e.g., tumor cells) toward drugs by inhibiting the ability of cancer cells to develop resistance to drugs. One of skill in the art can readily determine the particular hydrophobic agent (e.g., anti-cancer agent) to be included in the nanoparticles based on the disease or disorder to be treated or prevented. Preferably, the disease or disorder is cancer, such as lung cancer, breast cancer, prostate cancer, head and neck cancer, ovarian cancer, skin cancer, testicular cancer, pancreatic cancer, esophageal cancer, colorectal cancer, kidney cancer, cervical cancer, gastrointestinal cancer, and combinations thereof.

The nanoparticles or the composition thereof preferably are administered to the subject in a therapeutically effective amount. A therapeutically effective amount refers to an amount of the nanoparticles necessary to treat or prevent the particular disease or disorder. For example, when the nanoparticles comprise an anti-cancer agent, a therapeutically effective amount refers to the amount of the nanoparticles comprising the anti-cancer agent necessary for the chemotherapeutic treatment of cancer, such as the inhibition of the proliferation, invasiveness, or metastasis of tumor cells, the inhibition of tumor growth, and/or the inhibition of the sensitivity of cancer toward drugs by inhibiting the ability of cancer cells to develop resistance to drugs. The appropriate dose of the nanoparticles or composition thereof depends on the particular anti-cancer agent encompassed in the hydrophobic center of the nanoparticles and/or the particular TM peptide forming the nanoparticles.

Any route of administration can be used to deliver the nanoparticles to the subject. Suitable administration routes include intramuscular injection, transdermal administration, inhalation, topical application to tissue (e.g., tumor tissue), intratumoral administration, and parenteral administration (e.g., intravenous, peritoneal, intraarterial, subcutaneous, rectal, or vaginal, administration). An appropriate administration route easily can be determined by the physician or researcher. Subcutaneous administration can result in slow diffusion of nanoparticles from the site of injection, wherein intravenous administration can result in a quick spread of nanoparticles and quick clearance through the kidneys.

The following examples further illustrate the invention but, of course, should not be construed as in any way limiting its scope.

Example 1

This example demonstrates that the nanoparticles of the invention have uniform shape and diameter.

Peptides comprising the amino acid sequences of SEQ ID NO: 1, SEQ ID NO: 2, SEQ ID NO: 3, SEQ ID NO: 4, and SEQ ID NO: 5 were synthesized. Additionally, a peptide comprising the amino acid sequence of Leu-Leu-Phe-Val-Ile-Thr-Leu-Pro-Phe-Trp-Ala-Val-Asp-Ala-Val-Ala-Asn-Trp-Tyr-Phe-Gly-Asn-Lys-Lys (SEQ ID NO: 6), which replaces the two negatively charged aspartate residues at the end of SEQ ID NO: 1 with two positively charged lysine residues, was synthesized.

Peptides were solubilized in DMSO to yield 32 mg/ml solution. DMSO stocks were diluted with phosphate buffered saline (PBS) to produce 0.05-0.5 mg/ml solutions. Two μl of a sample were applied directly on microscopy grids, air-dried, stained with 0.5% (w/v) osmium tetroxide ($OsO_4$), and visualized with a Hitachi H-7000 electron microscope.

All peptides with a negatively charged end produced small nanoparticles (4-15 nm in diameter) as demonstrated by transmission electron microscopy. However, the nanoparticles formed higher order aggregates. The morphology of higher order structures differed for different sequences and showed a significant degree of variability.

Substitution of negative charges with positive charges (as in SEQ ID NO: 6) resulted in the formation of much large particles with highly variable diameters. Thus, the presence of negatively charged residues on one terminus of the TM peptides results in the formation of nanoparticles of relatively uniform shape and diameter.

Example 2

This example demonstrates that addition of hydrophilic oligomers affects nanoparticle aggregation.

Hydrophilic oligomers were added to a TM peptide with the amino acid sequence of SEQ ID NO: 1 to form the following: SEQ ID NO: 1-PEG11; SEQ ID NO: 1-PEG27; SEQ ID NO: 1-PEG38; and SEQ ID NO: 1-GGGGG.

To form peptides with hydrophilic oligomers (e.g., PEG), Fmoc amide resin (Applied Biosystem) was deprotected on an ABI433 peptide synthesizer. One gram of Fmoc-NH-$(PEG)_{11}$-COOH (NovaBiochem) or Fmoc-NH-$(PEG)_{27}$-COOH (NovaBiochem) were dissolved in 10 ml N-methyl-2-pyrrolidone (NMP) and activated by the addition of equimolar amounts of a 0.5 M solution of HBTU/HOBt (O-benzotriazole-N,N,N',N'-tetramethyl-uronium-hexafluoro-phosphate/1-hydroxy-benzotriazole) in dimethylformamide (DMF). Deprotected resin (80% moles in relationship to PEG) were added to the activated PEG and left on a shaker for 18 hours. For longer PEG molecules, like Fmoc-NH-$(PEG)_{38}$-COOH, the procedure was repeated starting from deprotection on the synthesizer. PEG38 was obtained by sequential coupling of PEG11 and PEG27. The resin with the PEG molecule of desired length was washed with NMP and dichloromethane, dried, and used for subsequent construction of TM domain chains by solid phase peptide synthesis on a 433A Applied Biosystems Peptide Synthesizer equipped with a conductivity monitoring unit utilizing Fmoc amino acid derivatives. Since all peptides contain Asp residues that are prone to aspartamide formation upon piperidine treatment during deprotection, the synthesizer was reprogrammed to use 50% piperidine in NMP containing 0.25 M HOBt. Solvent delivery times were calibrated to achieve a final concentration of HOBt of 0.1 M during deprotection.

The addition of HOBt completely prevented aspartamide formation that is usually accompanied by the appearance of products with −18 and +60 (piperidine additive) molecular masses on mass spectra. Peptides were cleaved from the resin with 87.5% trifluoroacetic acid containing 5% water, 5% thioanisol, and 2.5% triisopropylsilane (TIS), precipitated with cold diethyl ether, washed five times with ether, and dried in vacuum overnight. Peptides dissolved in DMF were purified by HPLC on a preparative (19×250 mm) Atlantis C3 reverse phase column (Agilent, Palo Alto, Calif.) in a gradient of 0.05% trifluoroacetic acid in water and acetonitril containing 0.05% trifluoroacetic acid. The fractions were analyzed by ion-spray LC/MS on an Agilent 1100 series instrument (Agilent, Palo Alto, Calif.) with the use of Zobax C3 Poroshell column and a gradient of 0.1 acetic acid in water and acetonitril. Only fractions containing more than 95% pure product were combined and freeze-dried. The purity and structure were further confirmed by ion-spray LC/MS with separation on a Zorbax C3 analytical column.

Polyglycine oligomers of desired length were assembled on the peptide synthesizer by step-wide synthesis utilizing standard Fmoc-protocol with HBTU/HOBt activation. Pre-loaded Gly-resin (Applied Biosystems) was used in the synthesis.

To determine the influence of hydrophilic tail length on nanoparticle aggregation, the degree of aggregation was determined by multi-angle light scattering for TM peptides with the amino acid sequences of SEQ ID NO: 1; SEQ ID NO: 1-PEG11; SEQ ID NO: 1-PEG27; SEQ ID NO: 1-PEG38; and SEQ ID NO: 1-GGGGG.

The peptides were dissolved in DMSO and diluted with 0.1 M Tris-HCl buffer (pH 7.2) to provide 0.4 mg/ml peptide solutions. This was used for further dilutions. The final concentration of DMSO was either 2.5% or 1.25% (kept constant for all dilutions in the series). The samples were sonicated at maximum intensity for 10 minutes and left at room temperature overnight (about 20 hours before measurements). The following day, the samples were centrifuged at 13200 rpm for 30 minutes.

Light scattering (LS) studies were performed by a DAWN EOS multi-angle detector (Wyatt Technology Corp., Santa Barbara, Calif.) at a laser wavelength of 690 nm. The LS detector was connected with an Agilent 1100 HPLC system (Agilent Technologies, Palo Alto, Calif.). The MALS detector was calibrated with HPLC grade toluene, 99.8% (Aldrich Chemicals, Milwaukee, Wis.), which was filtered through a 0.02 µM Anotop-25 inorganic membrane filter and then normalized with albumin (bovine) 98% monomer (Sigma Chemicals, St. Louis, Mo.). The data were collected and processed using Astra software (Wyatt Technology Corp.; version 4.90.04).

To determine the molecular weight of the peptide aggregates and the aggregation state, LS micro-batch measurements were performed. In brief, solvent was delivered through the HPLC system, bypassing the column compartment, at a flow rate of 0.05 ml/min. 900 µl samples with different peptide concentrations were injected through the HPLC autosampler. Four peptide concentrations were analyzed (i.e., 0.05 mg/ml, 0.1 mg/ml, 0.2 mg/ml, and 0.4 mg/ml). The concentrations were determined from weight measurements, since strong light scattering made traditional UV-absorbance determination inaccurate. The LS signal was collected for each concentration. Molecular weight was determined for each concentration separately using Astra software with a Debye plot and the Zimm equation. A single slice of collected signal giving the smallest error was chosen for molecular weight calculation at each concentration.

The results are set forth in Table 1.

TABLE 1

Influence of hydrophilic tail length on nanoparticle aggregation.

| | 0.05 mg/ml | | 0.1 mg/ml | | 0.2 mg/ml | | 0.4 mg/ml | |
|---|---|---|---|---|---|---|---|---|
| Peptide | MW (g/mol) | N | MW (g/mol) | N | MW (g/mol) | N | MW (g/mol) | N |
| SEQ ID NO: 1 | 11,400,000 ± 40,000 | 4090 | 6,906,000 ± 22,000 | 2478 | 6,952,000 ± 22,000 | 2494 | n/a | n/a |
| SEQ ID NO: 1-PEG11 | 2,515,000 ± 69,000 | 743 | 1,069,000 ± 20,000 | 316 | 463,800 ± 6,800 | 137 | 183,200 ± 900 | 54 |
| SEQ ID NO: 1-PEG27 | 1,171,000 ± 190,000 | 286 | 719,400 ± 100,700 | 176 | 682,000 ± 105,000 | 167 | 367,100 ± 38,400 | 90 |
| SEQ ID NO: 1-PEG38 | n/a | n/a | 436,100 ± 20,300 | 93 | 90,950 ± 9,210 | 19 | 110,500 ± 5,600 | 24 |
| SEQ ID NO: 1-GGGGG | 4,957,000 ± 8,000 | 1614 | 2,041,000 ± 4,000 | 664 | 865,600 ± 2,700 | 282 | 169,700 ± 300 | 55 | wherein N is a degree of aggregation (molecules per particle).

As illustrated by the data set forth in Table 1, the aggregation of nanoparticles decreased with increased length of PEG. Both types of hydrophilic tails (i.e., PEG and polyamino acid) were effective in reducing aggregation of the nanoparticles. PEG was less effective than polyglycine of comparable lengths. In addition, polyamino acid extensions are advantageous since they are biodegradable, thus providing more flexibility in fine-tuning the ability of nanoparticles to fuse with cellular membranes.

Additionally, structure-activity studies conducted on nanoparticles targeting drug resistance-associated transporter ABCG2 suggested that extension of the PEG length beyond 27 units compromised the biological activity of the peptide inhibitor, presumably interfering with membrane fusion. Consequently, the ideal nanoparticle with dual activity has a hydrophilic tail of sufficient length to prevent formation of large superstructures, but the tail should be reduced in size (degraded) in the target tissue (e.g., tumors) to allow for membrane fusion, so that the TM peptide forming the nanoparticle can exert its inhibitory effect (e.g, inhibiting drug resistance of cancer cells, inhibiting the growth of blood vessels in a tumor's environment, or inhibiting the movement of tumor cells) on the target membrane protein and the incorporated hydrophobic agent (e.g., cytotoxic drug) can be released.

Example 3

This example demonstrates that the length of the TM peptides affects nanoparticle aggregation.

To determine the influence of TM peptide length on nanoparticle aggregation, the degree of aggregation was determined by multi-angle light scattering for TM peptides of SEQ ID NO: 1-PEG27; SEQ ID NO: 7-PEG27; SEQ ID NO: 8-PEG27; and SEQ ID NO: 9-PEG27. SEQ ID NOs: 7, 8, and 9 are related to SEQ ID NO: 1 as deletion mutants, wherein SEQ ID NO: 7 lacks the two N-terminal amino acid residues of SEQ ID NO: 1, SEQ ID NO: 8 lacks the five N-terminal amino acid residues of SEQ ID NO: 1, and SEQ ID NO: 9 lacks the twelve N-terminal amino acid residues of SEQ ID NO: 1. The peptides were formed as described in Example 2.

The results are set forth in Table 2.

TABLE 2

| Influence of the transmembrane part length on nanoparticle aggregation. | | | | | | | | |
|---|---|---|---|---|---|---|---|---|
| | 0.05 mg/ml | | 0.1 mg/ml | | 0.2 mg/ml | | 0.4 mg/ml | |
| Peptide | MW (g/mol) | N | MW (g/mol) | N | MW (g/mol) | N | MW (g/mol) | N |
| SEQ ID NO: 1-PEG27 | 1,171,000 ± 190,000 | 286 | 719,400 ± 100,700 | 176 | 682,000 ± 105,000 | 167 | 367,100 ± 38,400 | 90 |
| SEQ ID NO: 7-PEG27 | 1,559,000 ± 245,000 | 403 | n/a | n/a | 219,000 ± 29,400 | 57 | 534,000 ± 61,300 | 138 |
| SEQ ID NO: 8-PEG27 | n/a | n/a | 29,550 ± 4,630 | 9 | 32,660 ± 6,730 | 10 | 34,520 ± 7,850 | 10 |
| SEQ ID NO: 9-PEG27 | No particle formation | 1 | No particle formation | 1 | No particle formation | 1 | No particle formation | 1 | wherein N is a degree of aggregation (molecules per particle).

As illustrated by the data set forth in Table 2, nanoparticle aggregation decreases with the decreased length of the TM peptide. However, peptides with the TM portion truncated to 11 amino acid residues failed to self-assemble into nanoparticles.

Example 4

This example demonstrates cellular and tumor uptake of the nanoparticles in tumor tissue.

A CXCR4-TM domain 2-derived pegylated peptide labeled with Alexa546 fluorescent dye was prepared. The following sequence was synthesized: SEQ ID NO: 1-Peg11-Hcy-Peg27, where Hcy stands for homocysteine. The peptide was reacted with 2-fold excess of Alexa546 5-maleimide (Invitrogen) in DMSO (at 128 mg/ml concentration) overnight and purified on a preparative (19×250 mm) C3 column. Ten µl of peptide were diluted with 630 µl PBS (to produce 2 mg/ml peptide solution), sonicated for 10 minutes, and used for intratumoral injection.

Nude mice were inoculated in a breast pad with one million MDA-231 breast cancer cells. Six weeks later, when tumor sizes reached about 5 mm in diameter, 0.1 ml of 2 mg/ml solution of the fluorescent nanoparticles in PBS were injected into a breast pad near the tumor.

Whole animals and excised tumors were imaged utilizing the Maestro 420 In-Vivo Spectral Imaging System (Cambridge Resources and Instrumentation, Inc.). The results showed that nanoparticles do not spread far from the injection site, but effectively penetrate tumor vasculature. In whole animals, 30 minutes after injection, the nanoparticles were localized to tumor tissue. Similarly, after 24 hours, the nanoparticles were localized to the tumor tissue without spreading from the injection site. Analysis of tumors excised 24 hours after injection indicated that the nanoparticles effectively penetrate tumor vasculature.

These results confirm that the nanoparticles of the invention can be used to deliver hydrophobic drugs, such as anticancer drugs, to target tissue, such as tumor tissue.

Example 5

This example demonstrates that nanoparticles constructed from the TM domains of certain receptors (e.g., CXCR4) and transporters have their own biological activity and can inhibit metastasis.

One million MDA-MB-231 breast cancer cells were injected in nude mice intraveneously on Day 0. On Day 1 and continuing twice weekly, mice were intraperitoneally injected with (1) 3 mg/kg of nanoparticles of the TM peptide of SEQ ID NO: 1-PEG27 dissolved in PBS; (2) 12 mg/kg of nanoparticles of the TM peptide of SEQ ID NO: 1-PEG27 dissolved in PBS; or (3) a control (PBS only).

All animals in the control group that were sacrificed or died naturally had numerous lung tumors. As set forth in FIG. 3, animals in the control group had only about 20% survival by Day 75. In contrast, there was about 40% survival by Day 75 in animals administered 3 mg/kg of nanoparticles. There was 100% survival by Day 75 in all of the animals administered 12 mg/kg of nanoparticles, and these animals continued to gain weight, which is indicative of a lack of metastasis.

While there were no surviving animals in the control group or in animals administered 3 mg/kg of nanoparticles by Day 91, a significant number of the animals administered 12 mg/kg of nanoparticles survived until the end of the experiment (Day 140), indicating that the administration of nanoparticles can significantly delay lung metastasis and prolong survival in a mouse model of breast cancer.

These results confirm that nanoparticles constructed from the TM domains of certain receptors (e.g., CXCR4) can inhibit metastasis.

Example 6

This example demonstrates the ability of nanoparticles of the invention to associate with hydrophobic agents in aqueous solution.

Nanoparticles formed from a portion of a TM domain targeting the CXCR4 receptor were tested for the ability to associate with solublized hydrophobic cytotoxic agents. Imidazoacridones and bisimidazoacridones were used because these anti-tumor agents are poorly soluble in aqueous solutions and possess fluorescence that is environment-sensitive (see Tarasov et al., *Photochem. Photobiol.*, 70(4): 568-578 (1999)). Specifically, HKA40A, a 1.8-naphthalimide imidazo(4,5,1-de)acridone derivative with potent anti-tumor activity (see U.S. Pat. No. 6,664,263) and WMC77, an imiazoacridone (5-{3-[4-(aminopropyl)-piperazin-1-yl]-propylamino}-2,10b-diaza-aceanthrylen-6-one) with fluorescence properties that are environment-sensitive (see U.S. Pat. No. 6,187,775), were used.

Visual inspection of a solution of 0.038 mg/ml of HKA40A yielded a clear, colorless liquid with an orange precipitate. In contrast, the same concentration of HKA40A in a solution of 0.4 mg/ml nanoparticles (SEQ ID NO: 1-PEG27) in PBS produced a clear, yellow solution with no precipitation.

Figure 1:
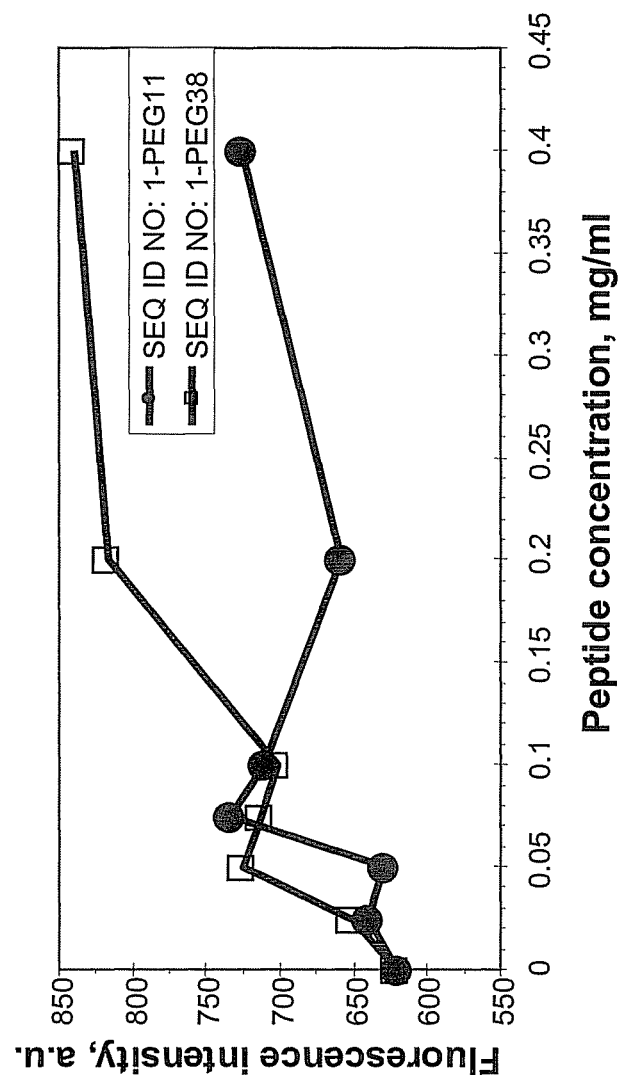
FIG. 1 is a graph of fluorescence emission intensity (a.u.) versus concentration (mg/ml) of nanoparticles comprising SEQ ID NO: 1-PEG11 (represented by circles) or SEQ ID NO: 1-PEG38 (represented by open squares).
Figure 2:
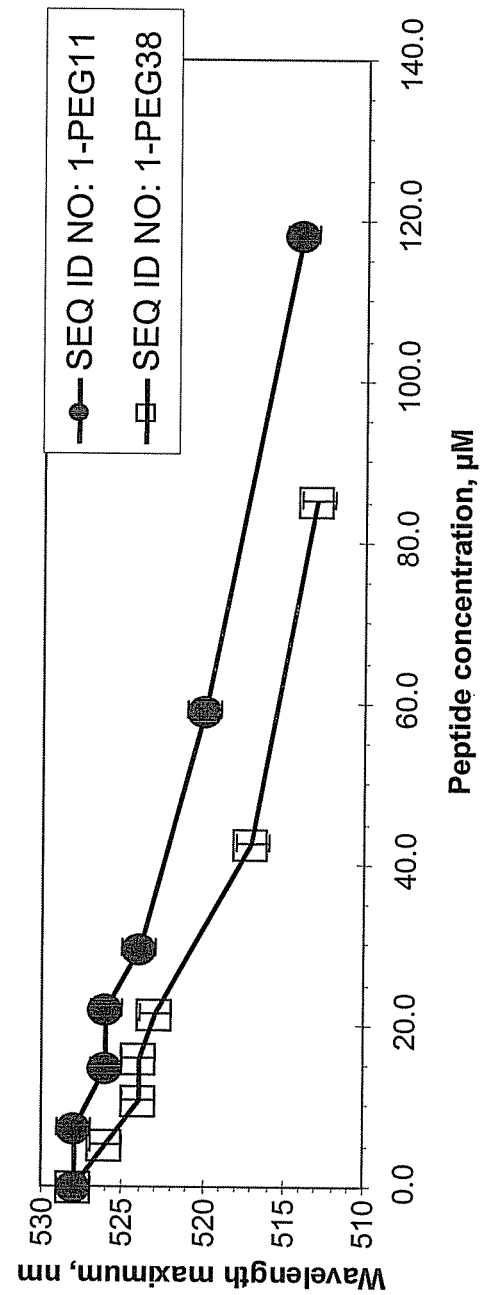
FIG. 2 is a graph of wavelength maximum (nm) versus concentration (µM) of nanoparticles comprising SEQ ID NO: 1-PEG11 (represented by circles) or SEQ ID NO: 1-PEG38 (represented by open squares).

Various amounts of nanoparticles (SEQ ID NO:1-PEG11 or SEQ ID NO 1-PEG38) were added to solutions of WMC77. The fluorescence emission intensity and shift in emission maxima were measured with the results depicted in FIGS. 1 and 2. The results reflected an increase in fluorescence emission intensity and a shift in emission maxima with increasing amounts of the nanoparticles, which is indicative of fluorophore transfer into a hydrophobic environment.

Furthermore, as demonstrated by the data in Table 3, when WMC77 (final concentration of 300 nM) was mixed with Alexa 546-labeled nanoparticles (which were produced as set forth in Example 4), fluorescence energy transfer was observed that indicated a close interaction between nanoparticles and WMC77.

TABLE 3

Fluorescence intensity of WMC77 solutions.

| Addititve | Fluorescence Intensity (a.u.) |
| --- | --- |
| No TM peptide | 622 |
| TM peptide | 726 |
| TM peptide-Alexa conjugate | 295 |

These experimental results confirm that the nanoparticles of the invention associate with hydrophobic agents in aqueous solution and provide the agents with a hydrophobic environment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing nanoparticles, which method comprises:
   (a) combining (i) an aqueous solution and (ii) an isolated peptide consisting of about 20 to about 25 amino acids of a transmembrane domain of CXCR4, wherein the carboxyl terminus of the peptide has 2 or 3 consecutive negatively charged residues,
   (b) adding a hydrophilic oligomer to the terminus of the peptide that contains 2 or 3 negatively charged residues, and
   (c) allowing the peptide to self-assemble into nanoparticles having a uniform shape and diameter, and wherein the hydrophilic oligomer is polyethylene glycol (PEG) having 11 to 27 monomeric units.

2. A composition of nanoparticles produced by
(a) combining (i) an aqueous solution and (ii) an isolated peptide consisting of about 20 to about 25 amino acids of a transmembrane domain of CXCR4, wherein the carboxyl terminus of the peptide has 2 or 3 consecutive negatively charged residues,
(b) adding a hydrophilic oligomer to the terminus of the peptide that contains 2 or 3 negatively charged residues, and
(c) allowing the peptide to self-assemble into nanoparticles having a uniform shape and diameter, and
wherein the hydrophilic oligomer is polyethylene glycol (PEG) having 11 to 27 monomeric units.

3. The composition of claim 2, wherein the PEG is PEG11.

4. The composition of claim 2, wherein the PEG is PEG27.

5. The composition of claim 2, wherein the peptide further comprises a ligand that specifically binds a cell surface receptor that is overexpressed in a tumor cell.

6. The composition of claim 2, wherein the nanoparticles have a diameter of about 3 nm to about 50 nm.

7. The composition of claim 2, wherein the nanoparticles have a diameter of about 8 nm to about 20 nm.

8. The composition of claim 2, wherein the peptide comprises SEQ ID NO: 1.

9. The composition of claim 3, wherein the peptide comprises SEQ ID NO: 1.

10. The composition of claim 4, wherein the peptide comprises SEQ ID NO: 1.

11. A composition of nanoparticles produced by
(a) combining (i) an aqueous solution and (ii) an isolated peptide comprising the amino acid sequence of SEQ ID NO: 1,
(b) adding PEG-27 to the carboxyl terminus of the peptide, and
(c) allowing the peptide to self-assemble into nanoparticles having a uniform shape and diameter.

12. The composition of claim 11, wherein the peptide further comprises a ligand that specifically binds a cell surface receptor that is overexpressed in a tumor cell.

13. The composition of claim 11, wherein the nanoparticles have a diameter of about 3 nm to about 50 nm.

14. The composition of claim 11, wherein the nanoparticles have a diameter of about 8 nm to about 20 nm.

15. The composition of claim 11, wherein the isolated peptide consists of the amino acid sequence of SEQ ID NO: 1.

* * * * *